United States Patent
Cook et al.

(10) Patent No.: US 6,322,987 B1
(45) Date of Patent: Nov. 27, 2001

(54) CARBAMATE-DERIVATIZED NUCLEOSIDES AND OLIGONUCLEOSIDES

(75) Inventors: Phillip Dan Cook, Vista; Muthiah Manoharan, Carlsbad, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/688,394

(22) Filed: Oct. 16, 2000

Related U.S. Application Data

(62) Division of application No. 09/372,856, filed on Aug. 12, 1999, now Pat. No. 6,166,188, which is a division of application No. 08/713,742, filed on Sep. 13, 1996, now Pat. No. 6,111,085.

(51) Int. Cl.[7] .............................. C12Q 1/68; C07H 19/00; C07H 21/00; A01N 61/00; A01N 43/04

(52) U.S. Cl. ........................... 435/6; 536/22.1; 536/23.1; 536/24.3; 536/24.33; 536/25.3; 536/25.32; 514/1; 514/44

(58) Field of Search ................. 536/22.1, 23.1, 536/24.3, 24.33, 25.3, 25.32; 514/1, 44; 435/6

(56) References Cited

U.S. PATENT DOCUMENTS

| | | | |
|---|---|---|---|
| 3,687,808 | 8/1972 | Merigan, Jr. et al. | 195/28 |
| 4,469,863 | 9/1984 | Ts'o et al. | 536/27 |
| 4,476,301 | 10/1984 | Imbach et al. | 536/27 |
| 4,958,013 | 9/1990 | Letsinger | 536/27 |
| 5,023,243 | 6/1991 | Tullis | 514/44 |
| 5,034,506 | 7/1991 | Summerton et al. | 528/391 |
| 5,130,302 | 7/1992 | Spielvogel et al. | 514/45 |
| 5,134,066 | 7/1992 | Rogers et al. | 435/91 |
| 5,138,045 | 8/1992 | Cook et al. | 536/27 |
| 5,141,813 | 8/1992 | Nelson | 428/402 |
| 5,166,195 | 11/1992 | Ecker | 514/44 |
| 5,177,196 | 1/1993 | Meyer, Jr. et al. | 536/22.1 |
| 5,212,295 | 5/1993 | Cooke | 536/26.7 |
| 5,214,134 | 5/1993 | Weis et al. | 536/25.3 |
| 5,216,141 | 6/1993 | Benner | 536/27.13 |
| 5,223,618 | 6/1993 | Cook et al. | 544/276 |
| 5,242,906 | 9/1993 | Pagano et al. | 514/44 |
| 5,248,670 | 9/1993 | Draper et al. | 514/44 |
| 5,264,423 | 11/1993 | Cohen et al. | 514/44 |
| 5,264,562 | 11/1993 | Matteucci | 536/23.1 |
| 5,264,564 | 11/1993 | Matteucci | 536/23.1 |
| 5,321,131 | 6/1994 | Agrawal et al. | 536/25.34 |
| 5,359,044 | 10/1994 | Cook et al. | 536/23.1 |
| 5,359,051 | 10/1994 | Cook et al. | 536/26.7 |
| 5,378,825 | 1/1995 | Cook et al. | 536/25.34 |
| 5,399,676 | 3/1995 | Froehler | 536/23.1 |
| 5,405,939 | 4/1995 | Suhadolnik et al. | 530/322 |
| 5,432,272 | 7/1995 | Benner | 536/25.3 |
| 5,434,257 | 7/1995 | Matteucci et al. | 536/24.3 |
| 5,442,049 | 8/1995 | Anderson et al. | 536/24.5 |
| 5,455,233 | 10/1995 | Spielvogel et al. | 514/44 |
| 5,457,187 | 10/1995 | Gmeiner et al. | 536/25.5 |
| 5,457,189 | 10/1995 | Crooke et al. | 536/24.5 |
| 5,457,191 | 10/1995 | Cook et al. | 536/27.13 |
| 5,459,255 | 10/1995 | Cook et al. | 536/27.13 |
| 5,470,967 | 11/1995 | Huie et al. | 536/24.3 |
| 5,484,908 | 1/1996 | Froehler et al. | 536/24.31 |
| 5,489,677 | 2/1996 | Sanghvi et al. | 536/22.1 |
| 5,495,009 | 2/1996 | Matteucci et al. | 536/25.3 |
| 5,502,177 | 3/1996 | Matteucci et al. | 536/26.6 |
| 5,506,351 | 4/1996 | McGee | 536/55.3 |
| 5,510,239 | 4/1996 | Baracchini, Jr. et al. | 435/6 |
| 5,514,577 | 5/1996 | Draper et al. | 435/238 |
| 5,514,788 | 5/1996 | Bennett et al. | 536/23.1 |
| 5,519,126 | 5/1996 | Hecht | 536/24.3 |
| 5,519,134 | 5/1996 | Acevedo et al. | 544/243 |
| 5,530,114 | 6/1996 | Bennett et al. | 536/24.3 |
| 5,539,389 | 7/1996 | Bystrak et al. | 340/825.52 |
| 5,541,307 | 7/1996 | Cook et al. | 536/23.1 |
| 5,543,507 | 8/1996 | Cook et al. | 536/23.1 |
| 5,576,925 | 11/1996 | Gorowitz et al. | 361/301.2 |
| 6,111,085 | 8/2000 | Cook et al. | 536/22.1 |
| 6,166,188 | 12/2000 | Cook et al. | 536/4.1 |

FOREIGN PATENT DOCUMENTS

| | | |
|---|---|---|
| 0 251 283 A2 | 1/1986 | (EP) . |
| WO 86/02929 | 5/1986 | (WO) . |
| WO 90/10448 | 9/1990 | (WO) . |

OTHER PUBLICATIONS

Asseline et al., "Nucleic acid–binding molecules with high affinity and base sequence specificity: Intercalating agents covalently linked to oligodeoxynucleotides", *Proc. Natl. Acad. Sci. USA*, 1984, 81, 3297–3301.

Atherton et al., "The Fluorenylmethoxycarbonyl Amino Protecting Group", *The Peptides*, Chapter 1, Gross and Meienhofer (eds.), Academic Press, New York, 1983, 9, 1–38.

Beaucage et al., "Advances in the Synthesis of Olitgonucletodies by the Phosphoramidite Approach", *Tetra. Letters*, 1992, 48, 2223–2311.

Bennett et al., "Cationic Lipids Enhance Cellular Uptake and Activity of Phosphorothioate Antisense Oligonucleotides", *Mol. Pharmacol.*, 1992, 41, 1023–1033.

Chollet, "Selective Attachment of Oligonucleotides to Interleukin 1β and Targeted Delivery to Cells", *Nucleosides & Nucleotides*, 1990, 9(7), 957–966.

Cohen, *Oligonucleotides: Antisense Inhibitors of Gene Expression*, CRC Press, Inc., Baca Raton, Florida, 1989.

Corey et al., "Sequence–Selective Hydrolysis of Duplex DNA by an Oligonucleotide–Directed Nuclease", *J. Am. Chem. Soc.*, 1989, 111, 8523–8525.

(List continued on next page.)

*Primary Examiner*—Jezia Riley
(74) *Attorney, Agent, or Firm*—Woodcock Washburn Kurtz Mackiewicz & Norris LLP

(57) ABSTRACT

Nucleosides and oligonucleosides functionalized to include carbamate functionality, and derivatives thereof. In certain embodiments, the compounds of the invention further include steroids, reporter molecules, reporter enzymes, lipophilic molecules, peptides or proteins attached to the nucleosides through the carbamate group.

4 Claims, No Drawings

OTHER PUBLICATIONS

Corey et al., "Generation of a Hybrid Sequence–Specific Single–Stranded Deoxyribonuclease", *Science*, 1987, 238, 1401–1403.

Delgardo et al., "The Uses and Properties of PEG–Linked Proteins", *Critical Rev. in Therap. Drug Carrier Systems*, 1992, 9(3,4), 249–304.

DeVos et al., "Solid Phase Non Isotopic Labelling of Oligodeoxynucleotides Using 5'–Protected Aminoalkyl Phosphoramidites: Application to the Specific Detection of Human Papilloma Virus DNA", *Nucleosides & Nucleotides*, 1990, 9(2), 259–273.

Dreyer et al., "Sequence–specific cleavage of single–stranded DNA: Oligodeoxynucleotide–EDTA Fe(II)", *Proc. Natl. Acad. Sci. USA*, 1985, 82, 968–972.

Gottikh et al., "Synthesis of Oligonucleotides Containing a Carboxyl Group at Either Their 5' End or their 3' End and Their Subsequent Derivatization by an Intercalating Agent", *Tetra. Letters*, 1990, 31(46), 6657–6660.

Guerra et al., "Synthetic 6–Glucosyl Phospholipid as a Drug Transport System", *Tetra. Letters*, 1987, 28(31), 3581–3584.

Haralambidis et al., "The Solid Phase Synthesis of Oligonucleotides Containing a 3'–Peptide Moiety", *Tetra. Letters*, 1987, 28(43), 5199–5202.

Haralambidis et al., "Preparation of base–modified nucleosides suitable for non–radioactive label attachment and their incorporation into synthetic oligodeoxyribonucleotides", *Nucl. Acid Res.*, 1987, 15(12), 4857–4876.

Hayakawa et al., "Allyl Protection in the Synthesis of Oligodeoxyribonucleotide Phosphorothioates", *Nucleosides & Nucleotides*, 1994, 13(6&7), 1337–1345.

Judy et al., "Facile Preparation of 3'Oligonucleotide–Peptide Conjugates", *Tetra. Letters*, 1991, 32(7), 879–882.

Krieg et al., "Uptake of Oligodeoxyribonucleotides by Lymphoid Cells is Heterogeneous and Inducible", *Antisense Res. and Dev.*, 1991, 1, 161–171.

Lemairte et al., "Specific antiviral activity of a poly(L–lysine)–conjugated oligodeoxyribonucleotide sequence complementary to vesicular stomatitis virus N protein mRNA initiation site", *Proc. Natl. Acad. Sci. USA*, 1986, 84, 648–652.

Leonetti et al., "Biological Activity of Oligonucleotide–Poly(L–lysine) Conjugates: Mechanism of Cell Uptake", *Bioconj. Chem.*, 1990, 1, 149–153.

Letsinger et al., "Cholesteryl–conjugated oligonucleotides: Synthesis, properties, and activity as inhibitors of replication of human immunodeficiency virus in cell culture", *Proc. Natl. Acad. Sci. USA*, 1989, 86, 6553–6556.

Manoharan et al., "2'–O–and 3'–O–Pyrimidine Aminotether–Containing Oligonucleotides: Synthesis and Conjugation Chemistry", *Tetra. Letters*, 1995, 36(21), 3647–3650.

Manoharan et al., "Lipidic Nucleic Acids", *Tetra. Letters*, 1995, 36(21), 3651–3654.

Miller et al., "A new approach to chemotherapy based on molecular biology and nucleic acid chemistry: Matagen (masking tape for gene expression)", *Anti–Cancer Drug Design*, 1987, 2, 117–128.

Nelson et al., "Bifunctional oligonucleotide probes synthesized using a novel CPG support are able to detect single base pair mutations", *Nucl. Acids. Res.*, 1989, 17(18), 7187–7193.

Ouchi et al., "Synthesis and Antitumor Activity of Poly(Ethylene Glycol)S Linked to 5–Fluorouracil Via a urethane or Urea Bond", *Drug Design and Disc.*, 1992, 9, 93–105.

Ramirez et al., "Nucleotidophospholipids: Oligonucleotide Derivatives with Membrane–Recognition Groups", *J. Am. Chem. Soc.*, 1982, 104, 5483–5486.

Ravasio et al., "Selective Hydrogenations Promoted by Copper Catalysis. 1. Chemoselectivity, Regioselectivity, and Stereoselectivity in the Hydrogenation of 3–Substituted Steroids", *J. Org. Chem.*, 1991, 56, 4329–4333.

Shea et al., "Synthesis, hybridization properties and antiviral activity of lipid–oligodeoxynucleotide conjugates", *Nuc. Acids Res.*, 1990, 18(13), 3777–3783.

Stepkowski et al., "Blocking of Heart Allograft Rejection by Intercellular Adhesion Molecule–1 Antisense Oligonucleotides Alone or in Combination with Other Immunosuppressive Modalities", *J. Immunol.*, 1994, 5336–5346.

Stirchak et al., "Uncharged Stereoregular Nucleic Acid Analogues. 1. Synthesis of a Cytosine–Containing Oligomer with Carbamate Internucleoside Linkages", *J. Org. Chem.*, 1987, 52, 4202–4206.

Telser et al., "Synthesis and Characterization of DNA Oligomers and Duplexes Containing Covalently Attached Molecular Lables: Comparison of Biotin, Fluorescein, and Pyrene Lables by Thermodynamic and Optical Spectroscopic Measurements", *J. Am. Chem. Soc.*, 1989, 111(18), 6966–6976.

Veber et al., "Isonicotinyloxycarbonyl, a Novel Amino Protecting Group for Peptide Synthesis", *J. Org. Chem.*, 1977, 42(20), 3286–3288.

Wachter et al., "A simple and efficient procedure for the synthesis of 5'–aminoalkyl oligodeoxynucleotides", *Nucl. Acids Res.*, 1986, 14(20), 7985–7994.

Weller et al., "Molecular Modeling of Acyclic Polyamide Oligonucleotide Analogues", *J. Org. Chem.*, 1991, 56, 6000–6006.

Yamana et al., "Synthesis and Interactive Properties of an Oligonucleotide with Anthraquinone at the Sugar Fragment", *Bioconjugate Chem.*, 1990, 1, 319–324.

Yamana et al., "Synthesis of Oligonucleotide Derivatives with Pyrene Group at Sugar Fragment", *Tetra. Letters*, 1991, 32(44), 6347–6350.

Zuckerman et al., "Site–Selective Cleavage of RNA by a Hybrid Enzyme", *J. Am. Chem. Soc.*, 1988, 110, 1614–1615.

Ali et al., "Synthesis of extended carbamate and urea linked thymidine dimers," *Nucleosides & Nucleotides*, 1996, 15(9), 1531–1543.

Conibear et al., "Measurement of nucleotide exchange kinetics with isolated synthetic myosin filaments using flash photolysis," *FEBS*, 1996, 380, 13–16.

Schirmeister et al., "The 2–(4–Nitrophenyl)ethoxycarbonyl(npeoc) and 2–(2,4–Dinitrophenyl(ethoxycarbonyl(d-npeoc) groups for protection of Hydroxy functions in ribonucleosides and 2'–deoxyribonucleosides," *Helv. Chim. Acta*, 1993, 76, 385–400.

Uhlmann, E. et al., "Antisense Oligonucleotides: A New Therapeutic Principle", *Chem. Revs.*, 1990, 90(4), 544–584.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 10 bases
        (B) TYPE: nucleic acid
        (C) STRANDEDNESS: single
        (D) TOPOLOGY: linear (xi) SEQUENCE DESCRIPTION: SEQ ID NO:1:

TTTTTTTTTU                                                            10

(2) INFORMATION FOR SEQ ID NO:2:

(i) SEQUENCE CHARACTERISTICS:
        (A) LENGTH: 10 bases
        (B) TYPE: nucleic acid
        (C) STRANDEDNESS: single
        (D) TOPOLOGY: linear (xi) SEQUENCE DESCRIPTION: SEQ ID NO:2:

TTTTTTTTTT                                                            10

(2) INFORMATION FOR SEQ ID NO:3:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:3:

TGCATCCCCC AGGCCACCCU                                                 20

(2) INFORMATION FOR SEQ ID NO:4:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:4:

TGCATCCCCC AGGCCACCAT                                                 20

(2) INFORMATION FOR SEQ ID NO:5:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:5:

TCGCATCGAC CCGCCCACTA                                                 20

(2) INFORMATION FOR SEQ ID NO:6:

(i) SEQUENCE CHARACTERISTICS:
        (A) LENGTH: 20 bases
        (B) TYPE: nucleic acid
        (C) STRANDEDNESS: single -continued

```
        (D) TOPOLOGY: linear (xi) SEQUENCE DESCRIPTION: SEQ ID NO:6:

CTGTCTCCAT CCTCTTCACT                                              20

(2) INFORMATION FOR SEQ ID NO:7:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:7:

CTGTCTCCAT CCTCACT                                                 17

(2) INFORMATION FOR SEQ ID NO:8:

(i) SEQUENCE CHARACTERISTICS:
        (A) LENGTH: 12 bases
        (B) TYPE: nucleic acid
        (C) STRANDEDNESS: single
        (D) TOPOLOGY: linear (xi) SEQUENCE DESCRIPTION: SEQ ID NO:8:

CCCAGGCUCA GA                                                      12
```

CARBAMATE-DERIVATIZED NUCLEOSIDES AND OLIGONUCLEOSIDES

This application is a division of U.S. patent application Ser. No. 09/372, 856, filed Aug. 12, 1999, now U.S. Pat. No. 6,166,188, which is a division of U.S. patent application Ser. No. 08/713,742, filed Sep. 13, 1996, now U.S. Pat. No. 6,111,085.

FIELD OF THE INVENTION

This application is directed to nucleosides, oligonucleotides and oligonucleosides that are functionalized with carbamate moieties. The carbamate moieties are used for linking various conjugate groups to the nucleosides, oligonucleotides or oligonucleosides. Suitable conjugate groups include, but are not limited to, steroids, reporter molecules, reporter enzymes, lipophilic molecules, cleaver molecules, peptides and proteins.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller, et al., *Anti-Cancer Drug Design* 1987, 2, 117) and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RMA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research reagents and therapeutic compounds. As research reagents oligonucleotides and oligonucleotide analogs find various uses including, but not limited to, probes and primers. For diagnostics, oligonucleotides and oligonucleotide analogs can be used in cell free systems, in vitro, ex vivo or in vivo. Currently a number of oligonucleotide based drugs are being tested in human clinical trials for various disease states including AIDS, against various cancers and for various systemic disease resulting from inappropriate immune responses. The antisense oligonucleotides and oligonucleotide analogs can be functionalized with various conjugate groups to modify certain of their properties. Thus reporter groups can be conjugated to the oligonucleotides or oligonucleotide analogs to assist in identification and location of the compounds in various testing medium including reagents, cellular products or digests, cell systems and organisms. Other conjugate groups can be utilized for transport, binding and uptake modulation, modification of solubility characteristics, analytical instrument identification and response and other useful properties known in the art.

Ramirez, et al., *J. Am. Chem. Soc.* 1982, 104, 5483, introduced the phospholipid group 5'-O-(1,2-di-O-myristoyl-sn-glycero-3-phosphoryl) into the dimer TpT independently at the 3' and 5' positions. Subsequently Shea, et al., *Nuc. Acids Res.* 1990, 18, 3777, disclosed oligonucleotides having a 1,2-di-O-hexyldecyl-rac-glycerol group linked to a 5'-phosphate on the 5'-terminus of the oligonucleotide. Certain of the Shea, et. al. authors also disclosed these and other compounds in patent application PCT/US90/01002. A further glucosyl phospholipid was disclosed by Guerra, et al., *Tetrahedron Letters* 1987, 28, 3581.

In other work, a cholesteryl group was attached to the inter-nucleotide linkage between the first and second nucleotides (from the 3' terminus) of an oligonucleotide. This work is disclosed in U.S. Pat. No. 4,958,013 and further by Letsinger, et al., *Proc. Natl. Acad. Sci. USA* 1989, 86, 6553. The aromatic intercalating agent anthraquinone was attached to the 2' position of a sugar fragment of an oligonucleotide as reported by Yamana, et al., *Bioconjugate Chem.* 1990, 1, 319. The same researchers placed pyrene-1-methyl at the 2' position of a sugar (Yamana et. al., *Tetrahedron Lett.* 1991, 32, 6347).

Lemairte, et al., *Proc. Natl. Acad. Sci. USA* 1986, 84, 648; and Leonetti, et al., *Bioconjugate Chem.* 1990, 1, 149). The 3' terminus of the oligonucleotides each include a 3'-terminal ribose sugar moiety. The poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A 35 disulfide linkage has also been utilized at the 3' terminus of an oligonucleotide to link a peptide to the oligonucleotide as is described by Corey, et al., *Science* 1987, 238, 1401; Zuckermann, et al., *J. Am. Chem. Soc.* 1988, 110, 1614; and Corey, et al., *J. Am. Chem. Soc.* 1989, 111, 8524.

Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1, 2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, et al., *Tetrahedron Letters* 1991, 32, 879. A similar commercial reagent (actually a series of such linkers having various lengths of polymethylene connectors) for linking to the 5'-terminus of are oligonucleotide is 5'-Amino-Modifier C6. These reagents are available from Glen Research Corporation (Sterling, Va.). These compounds or similar ones were utilized by Krieg, et al., *Antisense Research and Development* 1991, 1, 161 to link fluorescein to the 5'-terminus of an oligonucleotide. Other compounds of interest have also been linked to the 3'-terminus of an oligonucleotide. Asseline, et al., *Proc. Natl. Acad. Sci. USA* 1984, 81, 3297 described linking acridine on the 3'-terminal phosphate group of an poly (Tp) oligonucleotide via a polymethylene linkage. Haralambidis, et al., *Tetrahedron Letters* 1987, 28, 5199 report building a peptide on a solid state support and then linking an oligonucleotide to that peptide via the 3' hydroxyl group of the 3' terminal nucleotide of the oligonucleotide. Chollet, *Nucleosides & Nucleotides* 1990, 9, 957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer, et al., *Proc. Natl. Acad. Sci. USA* 1985, 82, 968. Fluorescein has been linked to an oligonucleotide in the same manner as reported by Haralambidis, et al., *Nucleic Acid Research* 1987, 15, 4857 and biotin in the same manner as described in PCT application PCT/US/02198. Fluorescein, biotin and pyrene were also linked in the same manner as reported by Telser, et al., *J. Am. Chem. Soc.* 1989, 111, 6966. A commercial reagent, Amino-Modifier-dT, from Glen Research Corporation (Sterling, Va.) can be utilized to introduce pyrimidine nucleotides bearing similar linking groups into oligonucleotides.

Carbamate linkages have been utilized to link conjugate groups to oligonucleotides at the 5' position as reported by DeVos, et al., *Nucleosides Nucleotides*, 9, 259, 1990, Wachter, et al., *Nucleic Acids Res.*, 14, 7985, 1986, and Gottikh, et. al., *Tetrahedron Lett.*, 31, 6657, 1990. Carbamate linkages have not been used for link conjugate groups to the 2' nor the 3' position of nucleosides, however, carbamate linkages have been used to form fixed length 3' to 5' internucleoside linkage as reported by Stirchak et al., *J. Org. Chem.*, 52, 4202, 1987.

While currently utilized nucleosides, nucleotides and oligonucleotides conjugate linking moieties certainly have great utility, there is a continuing need for improved conjugate linking groups have a potpourri of different properties. One such property is as a transitory blocking group during oligonucleotide synthesis. A further property is to provide a foundation at the 2' and 3' positions where "spacer" molecules of various lengths, e.g., diaminoalkyl groups such as 1,2-ethylene diamine and 1,6-diaminohexane, can be attached for modifying the spacing between the nucleosides, nucleotides or oligonucleotides and the conjugate group.

OBJECTS OF THE INVENTION

It is one object of this invention to provide nucleosides, oligonucleotides and oligonucleosides that include carbamate chemical functionalities.

It is a further object of the invention to provide compounds for linking various conjugate groups via carbamate linkages to nucleosides, oligonucleotides and oligonucleosides.

It is another object to provide compounds that include conjugated intercalators, nucleic acid cleaving agents, cell surface phospholipids, and/or diagnostic agents.

It is yet another object to provide improvements in research and diagnostic methods and materials for assaying bodily states in animals, especially disease states.

It is an additional object of this invention to provide therapeutic and research materials having modified or improved spectral, solubility, transfer or uptake properties for the identification and analysis of DNA and RNA, for the diagnosis of normal or disease states of cells, cellular components or organisms and treatment of diseases through various mechanisms including modulation of the activity of DNA or RNA.

BRIEF DESCRIPTION OF THE INVENTION

These and other objects are satisfied by the present invention, which provides compounds containing carbamate chemical functionalities. In one aspect, the invention provides oligonucleosides comprising a plurality of linked nucleosides, each of which includes a base portion and a ribofuranosyl sugar portion. In certain embodiments, at least one of such nucleosides bears at a 2'-O-position or a 3'-O-position a substituent having formula:

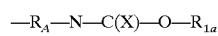

or

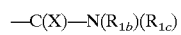

where:

$R_A$ is alkyl having from 1 to about 10 carbon atoms or $(CH_2-CH_2-Q)_x$;

$R_{1a}$ is alkenyl having 2 to about 10 carbon atoms;

$R_{1b}$ and $R_{1c}$, independently, are H, $R_2$, $R_A$, an amine protecting group or have formula $R_A-N(R_{1d})(R_{1e})$, $C(X)-R_2$, $C(X)-R_A-R_2$, $C(X)-Q-R_A-R_2$, or $C(X)-Q-R_2$;

$R_{1d}$ and $R_{1e}$, independently, are H, $R_2$, $R_A$, an amine protecting group or have formula $C(X)-R_2$, $C(X)-R_A-R_2$, $C(X)-Q-R_A-R_2$, or $C(X)-Q-R_2$;

$R_2$ is a steroid molecule, a reporter molecule, a lipophilic molecule, a reporter enzyme, a peptide, a protein, includes folic acid or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)$OR_A$, C(O)$R_4$, $R_A-N_3$, or $R_A-NH_2$;

$R_4$ is Cl, Br, I, $SO_2R_5$ or has structure:

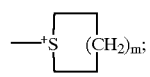

m is 2 to 7; and $R_5$ alkyl having 1 to about 10 carbon atoms.

In other embodiments, at least one of the nucleosides of the compounds of the invention includes a pyrimidine base portion which bears at its 5-position a substituent having formula:

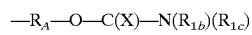

where $R_A$, X, $R_{1b}$, and $R_{1c}$ are as defined above.

The present invention also provides methods for inhibiting the expression of particular genes in the cells of an organism, comprising administering to said organism a compound according to the invention. Also provided are methods for inhibiting transcription and/or replication of particular genes or for inducing degradation of particular regions of double stranded DNA in cells of an organism by administering to said organism a compound of the invention. Further provided are methods for killing cells or virus by contacting said cells or virus with a compound of the invention. The compound can be included in a composition that further includes an inert carrier for the compound.

DETAILED DESCRIPTION OF THE INVENTION

This invention provides nucleosides, oligonucleotides and oligonucleosides containing carbamate chemical functionalities. The nucleoside subunits can be "natural" or "synthetic" moieties. Each nucleoside is formed from a naturally occurring or synthetic base and a naturally occurring or synthetic pentofuranosyl sugar group.

The term "oligonucleotide" refers to a polynucleotide formed from a plurality of linked nucleotide units. The nucleotides units each include a nucleoside unit. In the context of this invention, the term "oligonucleoside" refers to a plurality of nucleoside units that are linked together. In a generic sense, since each nucleotide unit of an oligonucleotide includes a nucleoside therein, the term "oligonucleoside" can be considered to be inclusive of oligonucleotides (i.e., nucleosides linked together via phosphate linking groups). In a further sense, the term "oligonucleoside" also refers to a plurality of nucleosides that are linked together via linkages other than phosphate linkages. The term "oligonucleoside" thus effectively includes naturally occurring species or synthetic species formed from naturally occurring subunits. For brevity, the term "oligonucleoside" will be used as encompassing both phosphate linked (oligonucleotides) and non-phosphate linked polynucleoside species.

Oligonucleosides according to the invention also can include modified subunits. Representative modifications include modification of a heterocyclic base portion of a nucleoside or a sugar portion of a nucleoside. Exemplary modifications are disclosed in the following U.S. Pat. Nos. 5,138,045, 5,212,295, 5,223,618, 5,359,051, 5,359,044, 5,378,825, 5,457,191, 5,459,255, 5,489,677, 5,506,351, 5,519,134, 5,541,307, 5,543,507, 5,130,302, 5,134,066, 5,432,272, 5,457,187, 5,484,908, 5,502,177, 5,216,141, 5,434,257 and 3,687,808. The disclosure of each of these patents is incorporated herein by reference.

The term oligonucleoside thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5- or 6-position; and purines having altered or replacement substituent groups at the 2-, 6-, or 8-positions. Representative modified sugars include carbocyclic or acyclic sugars, sugars having substituent groups at their 2'-position, and sugars having substituents in place of one or more hydrogen atoms of the sugar.

Altered base moieties or altered sugar moieties also include other modifications consistent with the spirit of this invention. Such oligonucleosides are best described as being structurally distinguishable from yet functionally interchangeable with naturally occurring or synthetic wild type oligonucleotides. All such oligonucleosides are comprehended by this invention so long as they function effectively to mimic the structure of a desired RNA or DNA strand.

The compounds of the present invention are those which bear a substituent having formula:

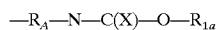

or

at a 2'-O— or 3'-O— nucleoside position or which bear a substituent having formula:

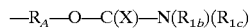

at a 5-pyrimidine position.

$R_A$ can be alkyl having from 1 to about 10 carbon atoms or $(CH_2-CH_2-Q)_x$, where Q is NH, O, or S and x is 1 to about 200, preferably 1 to about 50. Alkyl groups are substituents corresponding to branched and unbranched hydrocarbons. Preferred alkyl groups according to the invention have from 1, 2, or 6 carbon atoms.

$R_{1a}$ can be alkenyl having 2 to about 10 carbon atoms. Preferred alkenyl groups are those having 2 to about 5 carbon atoms. One particularly preferred alkenyl group is the 2-propenyl (i.e., $-CH_2CH=CH_2$) group.

$R_{1b}$, $R_{1c}$, $R_{1d}$, and $R_{1e}$, independently, can be H, $R_2$, $R_A$, an amine protecting group or have formula $R_A-N(R_{1d})(R_{1e})$, $C(X)-R_2$, $C(X)-R_A-R_2$, $C(X)-Q-R_A-R_2$, or $C(X)-Q-R_2$. In preferred embodiments, $R_{1b}$ (and/or $R_{1d}$) is H and $R_{1c}$ (and/or $R_{1e}$) is H, $R_2$, or $R_A$, or $R_{1b}$ and $R_{1c}$ (and/or $R_{1d}$ and $R_{1e}$), together, are a phthalimido amine protecting group. In other embodiments, $R_{1d}$ is H and $R_{1e}$ is $C(X)-Q-R_2$ where X is S or, preferably, O, and Q is NH, O, or S. $R_{1d}$ is H and $R_{1e}$ is $R_2$ or $C(X)-Q-R_2$.

$R_2$ is a steroid molecule, a reporter molecule, a lipophilic molecule, a reporter enzyme, a peptide, a protein, or has formula $-Q-(CH_2CH_2-Q-)_x-R_3$. In preferred embodiments, $R_2$ includes cholesterol or folic acid (i.e., includes a substantial portion of the cholesterol or folic acid molecule). For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Steroids include those chemical compounds that contain a perhydro-1,2-cyclopentanophenanthrene ring system. Proteins and peptides are utilized in their usual sense as polymers of amino acids. Normally peptides comprise such polymers that contain a smaller number of amino acids per unit molecule than do the proteins. Lipophilic molecules include naturally-occurring and synthetic aromatic and non-aromatic moieties such as fatty acids, esters, alcohols and other lipid molecules, substituted aromatic groups such as dinitrophenyl groups, cage structures such as adamantane and buckminsterful- lerenes, and aromatic hydrocarbons such as benzene, perylene, phenanthrene, anthracene, naphthalene, pyrene, chrysene, and naphthacene.

Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3-position of the cortisone rings. Particularly useful as reporter molecules are biotin, dinitrophenyl, and fluorescein dyes. Particularly useful as lipophilic molecules are steroid groups, alicyclic hydrocarbons, saturated and unsaturated fatty acids (such as palimitic and oleic), waxes, terpenes and polyalicyclic hydrocarbons including adamantane and buckminsterfullerenes. Particularly useful as reporter enzymes are alkaline phosphatase and horseradish peroxidase. Particularly useful as peptides and proteins are sequence-specific peptides and proteins including phosphodiesterase, peroxidase, phosphatase and nuclease proteins. Such peptides and proteins include SV40 peptide, RNaseA, RNase H and Staphylococcal nuclease. Particularly useful as terpenoids are vitamin A, retinoic acid, retinal and dehydroretinol.

Representative PEG groups are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249.

For use in antisense methodology, the oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorous-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., Tetrahedron 1992, 48, 2223 and references cited therein; and U.S. Pat. Nos. 3,687,808, 4,469,863, 4,476,301, 5,023,243, 5,034,506, 5,177,196, 5,214,134, 5,216,141, 5,264,423, 5,264,562, 5,264,564, 5,321,131, 5,399,676, 5,405,939, 5,434,257, 5,455,233, 5,476,925, 5,470,967, 5,495,009 and 5,519,126, as well as others of the above referenced patents. The disclosure of each of these patents is incorporated herein by reference.

It is preferred that the RNA or DNA portion which is to be modulated using oligonucleosides of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleoside for that portion.

In accordance with one preferred embodiment of this invention, the compounds of the invention can be targeted to various mRNA sequences including those disclosed in U.S. Pat. Nos. 5,166,195, 5,242,906, 5,248,670, 5,442,049, 5,457,189, 5,510,239, 5,514,577, 5,514,788, 5,539,389 and 5,530,114. The disclosure of each of these patents is incorporated herein by reference.

The nucleosides and oligonucleosides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

In preparing compounds of the invention, one or more protecting groups can be used for temporary blocking a chemically reactive site in the molecules. Protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including, but not: limited to: phthalimide (PHTH), trifluoroacetate (triflate) allyloxycarbonyl (Alloc), benzyloxycarbonyl (CBz) chlorobenzyloxycarbonyl, t-butyloxycarbonyl (Boc), fluorenylmethoxycarbonyl (Fmoc), and isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38).

Oligonucleosides according to the invention can bus assembled in solution or through solid-phase reactions, for example, on a suitable DNA synthesizer utilizing nucleosides according to the invention and/or standard nucleotide precursors. The nucleosides and nucleotide precursors can already bear alkylamino groups or can be later modified to bear such groups. Suitably protected nucleosides can be assembled into an oligonucleosides according to known techniques. See, e.g., Beaucage, et al., *Tetrahedron* 1992, 48, 2223.

Oligonucleosides according to the invention also can be prepared by assembling an oligonucleoside and appending an appropriate functionality thereto. For example, oligonucleosides having free hydroxyl groups can be assembled according to known techniques and then reacted with a reagent for linking the appropriate carbamate group thereto. As will be recognized, however, greater selectivity can be achieved in terms of placement of carbamate functionality within an oligonucleoside by introducing such functionality, as discussed above, on selected nucleosides and then using both the selected nucleosides and other nucleosides to construct an oligonucleoside.

Thus, the invention first builds the desired linked nucleoside sequence in the normal manner on the: DNA synthesizer. One or more (preferably two or more) of the linked nucleosides are then functionalized or derivatized with the lipophilic steroid, reporter molecule, lipophilic molecule, reporter enzyme, peptide or protein.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

2'-O-(N-ALLOC-6-AMINOHEXYL)-5'-O-DIMETHOXYTRITYL-5-METHYLURIDINE (COMPOUND 1)

2'-O-(6-Aminohexyl)-5'-O-dimethoxytrityl-5-methyluridine (1.98 g, 3 mmole, synthesized generally according to the procedure of Manoharan, et al., *Tetrahedron Lett.* 1995, 36, 3647 and *Tetrahedron Lett.* 1995, 36, 3651 using 5-methyl uridine in place of uridine) was coevaporated twice with anhydrous pyridine (2×25 mL) and the residue was dissolved in 3 mL of dry pyridine. Allyl-1-benzotriazolyl carbonate (720 mg, 3.3 mmole) was added to the pyridine solution and the reaction mixture was stirred at room temperature. Thin layer chromatography (TLC) analysis ($CH_3O:CH_2Cl_2$ 1:9) after 15 min. indicated the reaction was complete. The solvent was evaporated and the residue was purified by silica gel column chromatography using 2% $CH_3OH$ in $CH_2CH_2$. The yield was about 0.99 g (90%). The N-alloc protected compound was obtained as a white foam. $R_f=0.6$ in $CH_3OH:CH_2Cl_2$ 1:9.

EXAMPLE 2
DEPROTECTION OF ALLOC GROUP AT THE NUCLEOSIDE STAGE

The N-alloc compound prepared in Example 1 (7 mg, 0.1 mmol) was dissolved in 10 mL dry tetrahydrofuran (THF). To this solution 87 μL of morpholine (1 mmol) was added followed by tetrakis(triphenylphosphine)palladium (0) 15 mg (0.013 mmol). The reaction flask was covered with aluminum foil to protect it from light and was stirred. The reaction was followed by TLC analysis. After 6 hours, the reaction was complete, generating the amino nucleoside.

EXAMPLE 3
2'-O-(N-ALLYLOXYCARBONYL-6-AMINOHEXYL)-5'-O-DIMETHOXYTRITYL-5-METHYL URIDINE-3'-O-(2-CYANOETHYL)-N,N-DIISOPROPYL PHOSPHORAMIDITE (COMPOUND 2 ($T_2$*ALLOC PHOSPHORAMIDITE))

2'-O-(N-allyloxycarbonyl-6-aminohexyl)-5'-O-dimethoxytrityl-5-methyluridine (3 g, 4 mmol) was dissolved in 50 mL of anhydrous $CH_2Cl_2$. To this solution, 345 mg of diisopropylammonium tetrazolide (2 mmol) was added followed by 1.77 mL (5.0 mmol) of 2-cyanoethyl-N, N,N',N',-tetraisopropyl phosphorodiamidite. The reaction mixture was stirred at room temperature under argon atmosphere overnight. After 16 hours, TLC (hexane:ethylacetate 4:6) indicated conversion of the nucleoside into phosphoramidite. The reaction mixture was evaporated and the residue was applied onto a silica gel column and eluted with hexane:ethylacetate 4:6 ($R_f=0.42$). The product (2.3 g, 63%) showed two peaks around 154 ppm as expected for the phosphoramidite.

EXAMPLE 4
3'-O-(N-ALLYLOXYCARBONYL-6-AMINOHEXYL)-5'-O-DIMETHOXYTRITYI-URIDINE (COMPOUND 3)

3'-O-(6-Aminohexyl)-5'-O-dimethoxytrityl-uridine (6.46 g, 10 mmol, produced generally according to the procedure of Manoharan, et al., Tetrahedron Lett. 1995, 36, 3651) was coevaporated with dry pyridine (2×100 mL). The residue was dissolved in 100 mL of dry pyridine and to this solution allyl-1-benzotriazolyl carbonate (2.4 g, 11 mmol) was added and the reaction mixture was stirred for 1 hour. Pyridine was then evaporated and the residue was purified on a silica gel column using 2% $CH_3OH$ in $CH_2Cl_2$. The fractions containing the derived product were combined and evaporated to give a colorless foam (3.285 g, 45% yield). $R_f=0.53$ in $CH_3OH:CH_2Cl_2$ 9:1.

EXAMPLE 5
3'-O-(N-ALLYLOXYCARBONYL-6-AMINOHEXYL)-5'-DIMETHOXYTRITYL-URIDINE-2'-O-SUCCINYL-CONTROLLED PORE GLASS (COMPOUND 4 ($U_3$* ALLOC CPG))

In a 50 mL pear shaped flask 2.5 g succinylated control pore glass (CPG), 0.5 g of 3'-O-(N-allyloxycarbonyl-6-aminohexyl)-5'-dimethoxy uridine (0.69 mmol), 300 mg of dimethylaminopyridine, 800 mg of 1-(3-dimethylaminopropyl)ethyl carbodiimide (EDC), 20 mL of dry pyridine, and 1 mL of dry triethylamine were added and the flask was shaken in a wrist-action shaker for 24 hours. The solution was then filtered off and the CPG was washed with $CH_2Cl_2$, $CH_3OH$, $CH_2Cl_2$ and then with ether. It then was dried and transferred into a flask followed by the addition of 1.3 g pentachlorophenol, 300 mg of DMAP, 0.9 g of EDC, 20 mL of pyridine, and 0.5 mL of triethylamine. The flask was then shaken for 16 hours followed by the addition of 2.5 mL of piperidine. Shaking was continued for another 2 minutes during which period an intense yellow color developed in the reaction mixture. The CPG the was recovered by filtration, washed with pyridine, $CH_2Cl_2$, $CH_3OH$, $CH_2Cl_2$ and, finally, with ether. The CPG was then dried on a dessicator over $P_2O_5$. A 3.5 mg portion of the CPG was transferred to a 10 mL. volumetric flask. The loading on the CPG was determined to be 40 μmol/gm by addition of 3% trichloroacetic acid in $CH_2Cl_2$ and generating a trityl orange color.

EXAMPLE 6
OLIGONUCLEOTIDE SYNTHESIS WITH $T_2$*ALLOC PHOSPHORAMIDITE AND $U_3$* ALLOC CPG

The following oligonucleotides were synthesized using the $T_2$*alloc phosphoramidite and $U_3$*alloc CPG.

```
Oligomer I:    TTT TTT TTT U3*        (SEQ ID NO:1)

Oligomer II:   TTT TT2*T TTT T        (SEQ ID NO:2)

Oligomer III:  T2*GC ATC CCC CAG      (SEQ ID NO:3)
               GCC ACC CU3*

Oligomer IV:   T2*CA GU3*

Oligomer V:    T2*GC ATC CCC          (SEQ ID NO:4)
               CAG GCC ACC AT
```

Oligonucleotide phosphorothioates were synthesized on an Expedite synthesizer on a 4×1 μmol scale. The coupling time was extended for an additional minute. A double coupling step was employed when the modified amidite (Compound 2) or CPG (Compound 4) was used in the synthesis cycle. Trityl monitoring of the synthesis showed excellent coupling yields. The oligomers were not deprotected from CPG at this point.

EXAMPLE 7
DEPROTECTION OF ALLYLOXYCARBONYL GROUP IN THE SOLID SUPPORT

The CPG column containing 1 μmol of the synthesized oligomer I was transferred into a 5 mL pyrex screw-capped test tube. To this support were added 25 mg of $Pd_2$[PhCH=$CH_2$)$_2$.$CHCl_3$, $Ph_3P$ (64 mg) and 1 mL of n-butyl ammoniumformate (1.2M in THF prepared generally according to the procedure of Hayakawa, et al., *Nucleosides & Nucleotides* 1994, 13, 1337). The test tube was capped and heated for 1.5 hour at 50° C. during which the solution turned black. The supernatant then was discarded and the CPG was washed extensively with THF, acetone, a solution Df sodium N,N-diethyl-dithio carbamate (SDDTC, 0.1M in water, pH 9.78) for 10 min., acetone, water, acetone, SDDTC, water, acetone, $CH_2Cl_2$ and ether.

An aliquot of the alloc-deprotected CPG (10 mg) was placed in another pyrex screw-capped vial and deprotected with concentrated ammonia at 55° C. for 2 hours. The ammonia solution was evaporated to dryness in a speed vac and the residue was dissolved in 1 mL of water, filtered by centrifugation using a nylon-66 0.45 μ filter.

The resulting oligonucleotide was analyzed by analytical HPLC and mass spectrometry.

The other oligonucleotides (Oligomers II–V) were also deprotected according to the same protocol.

EXAMPLE 8
CONJUGATION OF PYRENE BUTYRIC ACID TO OLIGOMER I ON THE SOLID SUPPORT

Oligomer I-CPG (from which the allyloxy the allyloxycarbonyl group was removed in the solid support) was suspended in 2.5 mL of dimethylsulfoxide/pyridine (8:2, v/v). Pyrene butyric acid-N-hydroxysuccinimide ester (and 50 mg) was added to it in a reactor and the resulting mixture was shaken overnight. The DMSO/pyridine solution was filtered off and the CPG was washed with DMSO, $CH_2Cl_2$, and ether and then dried. The CPG then was deprotected in concentrated ammonia (2 mL) at 55° C. for 2 hours. The ammonia solution was then cooled and evaporated. The residue was dissolved in lmL of water and filtered. UV-vis spectral analysis indicated formation of pyrene conjugate which was confirmed by HPLC and mass spectral analysis.

EXAMPLE 9
HPLC AND MASS SPECTRAL ANALYSIS OF OLIOGMER I DERIVATIVES

| Modification | Retention Time[1] | Mass Spec. Expected | Mass Spec. Observed |
|---|---|---|---|
| Oligomer I 3'-O-(6-aminohexyl) | 34.7 | 3225.51 | 3225.01 |
| Oligomer I 3'-O-(N-alloc-6-aminohexyl) | 39.1 | 3309.55 | 3308.4 |
| Oligomer I 3'-O-(N-pyrene butyrate-6-aminohexyl) | 52.3 | 3495.86 | 3497.0 |

[1]HPLC conditions: Waters 600E with 991 detector; Waters Delta Pak C-18 column (3.9 × 300 mm) Solvent A: 50 mm TEAAc pH 7.0; B: 100% $CH_3CN$. 1.5 mL/min flow rate. Gradient: 5% B for first 10 minutes with linear increase in B to 40% during the next 50 minutes.

EXAMPLE 10
SOLUTION PHASE CONJUGATION OF PYRENEBUTYRIC ACID TO OLIGOMER II

Oligonucleotide II-CPG was deprotected as in Example 7 for alloc group in CPG and then in $NH_4OH$ to cleave the oligonucleotide from the solid support. The resultant oligonucleotide was dried and dissolved in 0.2M $NaHCO_3$ buffer (300 μL) and to this 50 mg of pyrene butyric acid-N-hydroxysuccinimide in 350 μl of DMF was added and the solution was allowed to stand at room temperature overnight. The solution was then passed through a Sephadex G-25 column to remove the excess pyrene reagent. The oligonucleotide was then analyzed by HPLC and mass spectral methods to establish the formation of pyrene conjugate.

HPLC And Mass Spectral Analysis Of Oligmer II And Its Conjugates

| Modification | HPLC Retention Time[1] | Mass Spec. Expected | Mass Spec. Observed |
|---|---|---|---|
| Oligomer II 2'-amine | 34.64 | 3239.54 | 3240.21 |
| Oligomer II 2'-alloc amine | 38.05 | 3323.58 | 3322.04 |
| Oligomer II 2'-pyrene | 47.10 | 3509.89 | 3507.18 |

[1]HPLC conditions: Waters 600E with 991 detector; Waters Delta Pak C-18 column (3.9 × 300 mm) Solvent A: 50 mm TEAAc pH 7.0; B: 100% $CH_3CN$. 1.5 mL/min flow rate. Gradient: 5% B for first 10 minutes with linear increase in B to 40% during the next 50 minutes.

EXAMPLE 11
CONJUGATION OF CHOLESTEROL To OLIGOMER V IN THE SOLID SUPPORT

Oligomer V-CPG (1 μmol) column is deprotected in the solid support as described in Example 7 and the solid support is washed once with pyridine/DMSO 2:8. Then 2.5 mL of DMSO/pyridine (8:2) is added to the CPG beads followed by 100 mg of cholesterol chloroformate. The solid support is shaken for 2 hours. Filtering the solvents, washing with $CH_2Cl_2$, $CH_3OH$, $CH_2Cl_2$ and ether gives the cholesterol modified oligonucleotide still bound to the CPG. It is then dried and deprotected with concentrated $NH_4OH$ to give the cholesterol conjugate.

EXAMPLE 12
3',5'-O-TETRAISOPROPYL-DISILOXANE-1,3-DIYL-$N^4$-BENZOYL-CYTIDINE-2'-O-(CARBONYLOXYSUCCINIMIDE) (COMPOUND 5)

3',5'-O-Tetraisopropyl disiloxane-1,3-diyl-$N^4$-benzoyl-cytidine was synthesized from $N^4$-benzoyl cytidine by treatment with 1,3-dichloro-1,1,3,3-tetraisopropyl 1,3-disiloxane and pyridine. $N^4$-benzoylcytidine (Chem-Impex, Wood Dale, Ill.) (5 g, 14.4 mmol) was coevaporated with pyridine (2×50 mL) and treated with 50 mL anhydrous pyridine and 5 g of 1,3-dichloro-1,1,3,-tetraisopropyl-1,3, disiloxane (15.85 mmol) under argon atmosphere. After 4 hours pyridine was evaporated and the residue was partitioned between $CH_2Cl_2$ and saturated $NaHCO_3$ solution. The organic layer was washed once with saturated NaCl solution and evaporated to give crude product of 3'-5'-O-tetraisopropyl disiloxane-1,3-diyl-$N^4$ benzoyl cytidine. The material was purified in a silica column (9:1 $C_2Cl_2/CH_3OH$) and eluted to give the pure compound (7.9 g, 93%) as a white foam.

3',5'-O-TIPS-$N^4$-benzoyl cytidine (5 g, 8.48 mmols) was dissolved in 25 mL of anhydrous acetonitrile and 25 mL methylene chloride. To this suspension N,N'-disuccinimidyl carbonate (3.6 g, 14 mmols) and triethylamine (25 mmol, 3.5 mL) were added. The resulting suspension was shaken in a wrist-action shaker until no starting material remained by TLC. The mixture was concentrated under reduced pressure and the residue was diluted with aqueous saturated $NaHCO_3$ solution (200 mL) and extracted thoroughly with methylene chloride (2×100 mL). The combined extracts were washed with saturated NaCl solution and dried over magnesium sulfate. Evaporation of the methylene chloride solution yielded the mixed carbonate which was used in further chemistry without any further purification (6.5 g yield).

EXAMPLE 13
CHOLESTERYL-OXYCARBONYL-AMINOHEXYLAMINE (COMPOUND 6)

Cholesteryl chloroformate (Fluka, 11.3 g, 25 mmol) was dissolved in 100 mL of anhydrous methylene chloride. This was added dropwise to 20 g (172 mmol) of 1,6-hexanediamine taken in 250 mL of pyridine:methylenechloride (1:1 v/v). The reaction mixture was stirred for 2 hours after which it was evaporated and extracted between methylene chloride (100 mL) and saturated NaHCO$_3$ solution (100 mL). The organic layer was washed one more time with saturated NaHCO$_3$ solution followed. by saturated NaCl solution, dried over anhydrous K$_2$CO$_3$, and evaporated to give the desired compound as a yellow waxy compound. $^{13}$C NMR showed (CDCl$_3$) one homogeneous compound, exhibiting both cholesterol and hexylamine carbon resonances.

EXAMPLE 14
2'-O-(CARBONYLAMINO-HEXYLAMINO-CARBONYL-OXYCHOLESTERYL)-3'-5'-O-TIPS-N$^4$-BENZOYL CYTIDINE (COMPOUND 7)

3,5'-TIPS-N$^4$-benzoyl-2'-O-(carbonyloxysuccinimidyl) cytidine (1 g, 1.41 mmol) was dissolved in CH$_2$Cl$_2$ (3 mL). To this solution was added cholesteryl-oxycarbonylaminohexylamine (1 g, 1.9 mmol) in methylene chloride (5 mL) containing triethylamine (2.2 mmol, 0.3 mL) and pyridine (0.5 mL) with stirring. The resulting mixture was stirred at room temperature until no mixed carbonate remained by TLC (4 hours). The reaction mixture was then diluted with CH$_2$Cl$_2$ (50 mL) and washed successively with saturated aqueous NaHCO$_3$ solution (50 mL), saturated NaCl solution and dried over MgSO$_4$. Removal of the solvent, followed by chromotography over silica gel 4:6 ethylacetate/hexanes afforded the carbamate (1.14 g, 0.99 mmol) in 70% yield.

EXAMPLE 15
5'-O-DIMETHOXYTRITYL-2'-O-(CARBONYLAMINOHEXYL AMINOCARBONYLOXY CHOLESTERYL)-N'-BENZOYL CYTIDINE (COMPOUND 8

3'-5'-O-TIPS-2'-O-(carbonylamino-hexylamino carbonyloxy, cholesteryl)-N$^4$-benzoyl-cytidine is treated with (nBu)$_4$NF in pyridine. The resultant 3'-5'-dihydroxy compound is treated, with dimethoxytrityl chloride/pyridine to give the corresponding 5'-O-dimethoxytrityl compound.

EXAMPLE 16
5'-O-(DIMETHOXYTRITYL)-2'-O-(CARBONYL-AMINOHEXYL-AMINOCARBONYL-OXY-CHOLESTERYL]N$^4$-BENZOYL-CYTIDINE-3'-O-[2-CYANOETHYL-N,N-DIISOPROPYL] PHOSPHORAMIDITE (COMPOUND 9)

5'-O-(Dimethoxytrityl)-2'-O-[carbonylaminohexyl-aminocarbonyloxy-N-(3-oxycarbonyl-cholesteryl)amino] N$^4$-benzoyl cytidine is dissolved in dry dichloromethane. 2-Cyanoethyl N,N,N',N'-tetraisopropylphosphorodiamidite and diisopropylammonium tetrazolide are added to the mixture, which is stirred under argon for 16 hours. Dichloromethane is added to the solution, washed with an equal volume of saturated NaHCO$_3$. The aqueous layer is washed with an equal volume of dichloromethane. The combined organic layers are washed with an equal volume of saturated NaCl and dried over MgSO$_4$ and concentrated in vacuo. The residue is chromatographed on a silica gel column with a gradient of 25% ethyl acetate in hexanes to 70% ethyl acetate to yield the amidate.

EXAMPLE 17
5'-O-(DIMETHOXYTRITYL)-2'-O-[CARBONYLAMINOHEXYL-N-(3-OXYCARBONYL-CHOLESTERYL) AMINO]N$^4$-BENZOYL-CYTIDINE-3-O-(SUCCINYL AMINOPROPYL)-CONTROLLED PORE GLASS (COMPOUND 10)

Succinylated and capped controlled pore glass (0.3 grams) is added to 2.5 ml anhydrous pyridine in a 15ml pear-shaped flask. DEC (0.07 grams, 0.36 mmol), TEA (100 μl, distilled over CaH$_2$), DMAP (0.002 grams, 0.016 mmol) and 5'-O-(dimethoxytrityl)-2'-O-[carbonylaminohexyl-N'-(3-oxycarbonyl-cholesteryl)amino]N$^4$-benzoyl cytidine are added under argon and the mixture shaken mechanically for 16 hours. More nucleoside (0.20 grams) is added and the mixture shaken an additional 18 hours. Pentachlorophenol (0.03 grams, 0.11 mmol) is added and the mixture shaken 9 hours. CPG is filtered off and washed successively with dichloromethane, triethylamine, and dichloromethane. CPG is then dried under vacuum, suspended in 10 ml piperidine and shaken 5 minutes. CPG is filtered off, washed thoroughly with dichloromethane and again dried under vacuum. The extent of loading is determined by spectrophotometric assay of dimethoxytrityl cation in 0.2 M p-toluenesulfonic acid at 498 nm as approximately 31 μmol/g.

EXAMPLE 18
OLIGONUCLEOTIDE SYNTHESIS

Oligonucleotides incorporating cholesterol carbamate nucleoside are synthesized in an Expedite Synthesizer. An extended coupling time is used for cholesterol building blocks.

| Oligomer VI | TGC* ATC CCC CAG GCC ACC AT |
| | (P = S) |
| | (SEQ ID NO:5) |
| Oligomer VII | TC*G CAT CGA CCC GCC CAC TA |
| | (P = S) |

C*= Compound 9 synthesized according to Example 16

The oligonucleotides are purified by standard HPLC protocols.

EXAMPLE 19
ASSAY FOR ICAM-1 USING 2'-CHOLESTEROL CONJUGATED OLIGONUCLEOTIDES MATERIALS

Cholesterol-oligonucleotide assays for ICAM-1 are done in the bEnd.3 cell line, a brain endotheliomausing Opti-MEM, trypsin-EDTA and DMEM with high glucose (all from Gibco-BRL, Grand Island, N.Y.), Dulbecco's PBS (Irvine Scientific, Irvine, Calif.), sterile, 12 well tissue culture plates and Facsflow solution (from Becton Dickinson, Mansfield, Mass.), ultrapure formaldehyde (Polysciences, Warrington, Pa.), recombinant human TNF-α (R&D Systems, Minneapolis, Minn., mouse interferon-γ (Genzyme, Cambridge, Mass.), and Fraction V, BSA (Sigma, St. Louis, Mo.). The mouse ICAM-1-PE, VCAM-1-FITC, hamster IgG-FITC and rat IgG2α-PE antibodies were purchased from Pharmingen (San Diego, Calif.). Zeta-Probe nylon blotting membrane was purchased from Bio-Rad (Richmond, Calif.). QuickHyb solution was purchased from Stratagene (La Jolla, Calif.). A cDNA labeling kit, Prime-a-Gene, was purchased from ProMega (Madison, Wis.). NAP-5 columns were purchased from Pharmacia (Uppsala, Sweden).

Oligonucleotide Treatment

Cells are grown to approximately 75% confluency in 12 well plates with DMEM containing 4.5 g/L glucose and 10% FES. Cells are washed 3 times with Opti-MEM pre-warmed to 37° C. Oligonucleotide VI is premixed with Opti-MEM, serially diluted to desired concentrations and transferred onto washed cells for a 4 hour incubation at 37° C. Media is removed and replaced with normal growth media with or without 5 ng/ml TNF-α and 200 U/ml interferon-γ, incubated for 2 hours for northern blot analysis of mRNA or overnight for flow cytometric analysis of cell surface protein expression.

Flow Cytometry

After oligonucleotide treatment, cells are detached from the plates with a short treatment of trypsin-EDTA (1-2 min.). Cells are transferred to 12×75 mm polystyrene tubes and washed with 2% BSA, 0.2% sodium azide in D-PBS at 4° C. Cells are centrifuged at 1000 rpm in a Beckman GPR centrifuge and the supernatant is then decanted. ICAM-1, VCAM-1 and the control antibodies are added at 1 ug/ml in 0.3 ml of the above buffer. Antibodies are incubated with the cells for 30 minutes at 4° C. in the dark, with gentle agitation. Cells are washed again as above and then resuspended in 0.3 ml of FacsFlow buffer with 0.5% ultrapure formaldehyde. Cells are analyzed on a Becton Dickinson FACScan. Results are expressed as percentage of control expression, which is calculated as follows: [((CAM expression for oligonucleotide-treated cytokine induced cells)–(basal CAM expression))/((cytokine-induced CAM expression)–(basal CAM expression))]×100. For the experiments involving cationic lipids, both basal and cytokine-treated control cells are pretreated with Lipofectin for 4 hours in the absence of oligonucleotides. (Bennett, et al., *Mol Pharmacol*. 1992, 41, 1023.)

RNA Isolation and Analysis

Total cellular RNA is isolated by cellular lysis in 4M guanidinium isothiocyanate followed by a CsCl gradient. Total cellular RNA is separated on a 1.2% agarose gel containing 1.1% formaldehyde, then transferred to the nylon membrane and UV crosslinked to the membrane using a Stratagene UV crosslinker 2400. Blots are hybridized with cDNA probes purified on NAP-5 columns that are random primed for 1 to 2 hours in QuickHyb solution. Blots are washed 2 times at 25° C. in 2×SSC with 0.1% SDS for 10 minutes each and then washed 1 time in 0.1% SSC with 0.1% SDS at 60° C. for 30 minutes.

EXAMPLE 20
EFFECT OF 2'-CHOLESTEROL CONJUGATED OLIGONUCLEOTIDE ON ICAM-1 EXPRESSION

The nucleoside-cholesterol conjugate (Compound 9) from Example 16 is incorporated into the antisense oligonucleotide developed for mouse model studies (ISIS 3082) disclosed by Stepkowski, et al., *J.Immunol*. 1994, 5337.)

Oligomer VI TGC* ATC CCC CAG GCC ACC AT (P=S)

The resultant conjugate (Oligomer VI) is tested for inhibiting ICAM-1 expression. ISIS-3082 shows antisense inhibition in cell culture with an IC$_{50}$ of 100 nM when formulated with a cationic lipid for delivery.

In cell culture comparison experiments evaluating the effect of ISIS-3082 and Oligomer VI on controlling ICAM-1 expression without any cationic lipid adjuvant, Oligomer VI inhibits ICAM-1 in a dose dependent manner. ISIS-3082 does not show any activity at all, even when high concentrations are used. Furthermore, the inhibition of protein expression appears to be target specific. When analyzed for controlling the isotype protein VCAM-1, neither molecule show significant inhibition of VCAM-1 expression. Since no sequence similarity exists between the mouse ICAM-1 sequence and the mouse VCAM-1 sequence, ISIS-3082 or its conjugate would not be expected to influence the expression of VCAM-1 if they are working through an antisense mechanism.

EXAMPLE 21
CHOLESTEROL CONJUGATION AFFECTS THE BIODISTRIBUTION OF THE OLIGONUCLEOTIDE

The effect of cholesterol conjugation on the pharmacokinetic properties of the oligonucleotide is determined in mice using $^3$H cadiolabeled Oligonucleotide VI. This modification shows a marked influence on the biodistribution of the oligonucleotide. ISIS-3082 is mainly distributed in liver, kidney, skeletal muscle and skin. In the case of Oligomer VI, more oligonucleotide is found in the liver. The amount is reduced in kidney, skeletal muscle and skin. Oligomer VI is also retained in the plasma for longer periods of time than is ISIS-3082 which is consistent with the improved efficacy of Oligomer VI.

EXAMPLE 22
INHIBITION OF ICAM-1 EXPRESSION IN MOUSE LIVER USING CHOLESTEROL CONJUGATED OLIGONUCLEOTIDES

Eight to twelve week old C57Bl/10 mice are injected twice intravenously with 10 mg/kg oligonucleotide at 24 hours and 2 hours before lipopolysaccharide (LPS) administration. A 25 ugs portion of LPS from *S. typhosa* (Difco Labs, Detroit, Mich.) is injected intraperitoneally and the mice are sacrificed 4 hours later. Total RNA from the liver is isolated and analyzed as described above. To determine if the increased delivery of oligonucleotides to liver correlated with increased efficacy, mice are treated with the ICAM-1 antisense oligonucleotides and then ICAM-1 expression is induced by treating with bacterial endotoxin (Lipopolysaccharides, LPS). Oligomer VI at a dose of 11 mg/kg reduces ICAM expression by 40–50% while unconjugated oligonucleotide failed to affect ICAM-1 expression. More importantly, increasing the dose of ISIS-3082 up to 100 mg/kg did not result in significant inhibition.

EXAMPLE 23
CORRELATION OF STABILITY WITH ACTIVITY AND SEQUENCE SPECIFIC ACTIVITY OF OLIGONUCLEOTIDES

The following compounds are evaluated: (I) deoxyphosphorothioate oligomer ISIS-3082; (ii) Oliogmer VI; (iii) Oligomer VII; and (iv) Oligomer VIII.

Two sets of in vitro experiments are carried out with these compounds: assay of ICAM-1 MRNA by Northern blot analysis and ICAM-1 protein cell-surface expression by FACS analysis in bEnd.3 cells. Ad protein inhibition, ISIS-3082 complexed with cationic lipids inhibited ICAM-1 expression with an IC$_{50}$ at 100 nm concentration. In the absence of cationic lipids, neither ISIS-3082 by itself, Oligomer VII, nor Oligomer VIII, cholesterol conjugate thereof, reduces ICAM-1 gene expression. These results establish that effects are sequence specific and prove the antisense mechanism of action.

EXAMPLE 24
3',5'-O-TIPS-N$^4$-BENZOYL-2'-O-(CARBONYLAMINO ETHYLENE DIAMINO)CYTIDINE (COMPOUND 11)

3', 5'-TIPS-N$^4$-benzoyl-2'-O-(carbonyloxy succinimidyl) cytidine (1 g, 1.41 mmol) was dissolved in CH$_2$Cl$_2$ (3 mL). To this solution 1.5 equivalents of ethylene diamine in CH$_2$Cl$_2$ was added very slowly with external cooling. A white turbidity was noticed. After 4 hours the solution was evaporated, separated between saturated NaHCO$_3$ solution and CH$_2$Cl$_2$ layers. The organic layer was washed with saturated NaCl solution dried over anhydrous magnesium sulfate and evaporated. The $^{13}$C NMR of the residue showed an ethylene diamine unit connected to 2'-position via a carbamate linkage.

EXAMPLE 25
N-(PHTHALIMIDO) ETHYLENEDIAMINE (PHTH-NH—CH$_2$—CH$_2$—NH$_2$) (COMPOUND 12)

One equivalent of phthalic anhydride is treated with 10 equivalents of ethylenediamine in CH$_2$Cl$_2$, under high dilu-

17 tion conditions. After checking for the product in TLC, the reaction mixture is evaporated and worked UD. The excess ethylene diamine is removed with aqueous layer leaving the monoalkylated product.

EXAMPLE 26
5'-O-DIMETHOXYTRITYL-$N^4$-BENZOYL-2'-O-[CARBONYLAMINO-N-PHTHALIMIDO ETHYLENEDIAMINE]-3'-O-(2-CYANOETHYL-N,N-DIISOPROPYL) PHOSPHORAMIDITE (COMPOUND 13)

3',5'-TIPS-$N^4$-benzoyl-2'-O-(carbonyloxy succinimidyl) cytosine is treated with N-phthalimido ethylenediamine. The resultant carbamate is treated with TRAF in THF to give the 3',5'-dihydroxycompound which is them dimethoxytritylated at the 5'-position with dimethoxytritylchloride/pyridine, The 5'-protected nucleoside is then phosphitylated as in Example 3.

EXAMPLE 27
5'-O-DIMETHOXYTRITYL-$N^4$-BENZOYL-2'-O-[CARBONYLAMINO-N-PHTHALIMIDO ETHYLENEDIAMINE]-5'-O-[SUCCINYL-AMINOPROPYL]CONTROLLED PORE GLASS (COMPOUND 14)

The 5'-O-dimethoxytrityl-nucleoside of Example 26 is attached to controlled pore glass as in Example 5 (rather than phosphitylated) to give the desired CFO,

EXAMPLE 28
5'-DIMETHOXYTRITYL-$N^6$-BENZOYL-2'-O-(CARBONYLAMINOETHYLENE (N-PHTHALIMIDO DIAMINE) ADENOSINE-3'-O-[2-CYANOEThYL-N,N'-DIISOPROPYL] PHOSPHORAMIDITE (COMPOUND 15)

5'-Dimethoxytrityl-$N^6$-benzoyl-3'-t-butyldimethylsilyl adenosine (Chem-Impex International, Wood Dale, Ill.) is converted to its succinimidyl carbornate at the 2'-position as in Example 14. Then the 3'-t-butyl-dimethylsilyl group is deprotected with (n-Bu)$_4$NF in pyridine. The resultant nucleoside is phosphitylated as in Example 16 to give the title compound.

EXAMPLE 29
5'-O-DIMETHOXYTRITYL-$N^6$-BENZOYL-2'-O-(CARBONYLAMINOETHYLENE(N-PHTHALIMIDO DIAMINE) ADENOSINE-3'-O-(SUCCINYLAMINOPROPYL)-CONTROLLED PORE GLASS (COMPOUND 16)

5'-O-Dimethoxytrityl-$N^6$-benzoyl-3'-t-butyldimethylsilyl adenosine (Chem-Impex International, Wood Dale, Ill.) is converted to its succinimidyl carbonate at the 2'-position as in Example 14. Then the 3'-t-butyl-dimethylsilyl group is deprotected with (NBu)$_4$NF in pyridine. The resultant nucleoside is converted to the corresponding controlled pore glass as in Example 17 to give the title compound.

EXAMPLE 30
5'-O-DIMETHOXYTRITYL-$N^6$-BENZOYL-3-O-[CARBONYLAMINOETYLENE (N-PHTHALIMIDO DIAMINE) ADENOSINE-2'-O-(SUCCINYLAMINOPROPYL)-CONTROLLED PORE GLASS (COMPOUND 17)

5'-O-Dimethoxytrityl-$N^6$-benzoyl-2'-t-butyldimethylsilyl adenosine (Chem-Impex International, Wood Dale, Ill.) is converted to its succinimidyl carbonate at the 3'-position as in Example 14. Then the 2'-t-butyldimethylsilyl group is deprotected with (NBu)$_4$NF in pyridine. The resultant nucleoside is attached to succinylated controlled pore glass as in Example 17.

18

EXAMPLE 31
5'-O-DIMETHOXYTRITYL-5-O-[METHYLENE-OXY-CARBONYLAMINOETHYL (N-PHTHALIMIDO) AMINE]-2'-DEOXYURIDINE (COMPOUND 18)

5'-O-Dimethoxy-5'-O-(hydroxy methyl) 2'-deoxyuridine (available from ChemGenes, Waltham, Mass.) is converted to 3'-benzoyl-5-O-(succinimidyl carbonate) by treatment with N,N-disuccinimidyl carbonate (as described in Example 12) and by further protection of the 3'-position. The resulting mixed carbonate is treated with 1.5 equivalents of N-phthalimido-amino ethyl amine (Phth-NH—CH$_2$—CH$_2$—NH$_2$) in CH$_2$Cl$_2$ containing triethylamine and pyridine. The reaction mixture is worked up as described in Example 14 to give the title compound.

EXAMPLE 32
5'-O-DIMETHOXYTRITYL 5-O-(METHYLENE -OXY-CARBONYLAMINOETHYL (N-PHTHALIMIDO) AMINO]-2'-DEOXYURIDINE-3'-O-[(CYANOETHYL)-N,N-DIISOPROPYL PHOSPHORAMIDITE (COMPOUND 19)

5 The nucleoside of Example 31 is phosphitylated using 2-cyanoethyl-N,N,N',N'-tetraisopropyl phosphorodiamidite and diisopropylammonium tetrazolide in CH$_2$Cl$_2$ solvent as described in Example 16. The phosphoramidite is purified in a silica column using 50:50 ethylacetate hexanes.

EXAMPLE 33
5'-O-DIMETHOXYTRITYL-5-O-METHYLENE-OXY-CARBONYLAMINOETHYL (N-PHTHALIMIDO) AMINO]-2'-DEOXYURIDINE-3'-O-(SUCCINYLAMINOPROPYL)-CONTROLLED PORE GLASS (COMPOUND 20)

The nucleoside from Example 30 is attached to succinylated CPG as described in Example 17. The loading is determined to be 36 µMols/g.

EXAMPLE 34
2'-CARBAMATE-AMINE LINKING GROUP CONTAINING PHOSPHODIESTER OLIGONUCLEOTIDES

Compound 15 was utilized in the DNA synthesizer as a 0.1M solution in anhydrous CH$_3$CN. Oligonucleotide synthesis was carried out in either an ABI 394 synthesizer employing the standard synthesis cycle with an extended coupling time of 10 minutes during coupling of Compound 15 into the oligonucleotide dequence. Coupling efficiency of >98% was observed for the coupling of the modified amidite.

The following oligonucleotides having phosphodiester inter-nucleotide linkages were synthesized:

```
Oligomer IX:  CTG TCT CCA* TCC TCT      (SEQ ID NO:6)
              TCA CT

Oligomer X:   CTG TCT CCA* TCC TCA* CT  (SEQ ID NO:7)
``` where A* represents a nucleotide functionalized with a carbamate-2'-aminolinker moiety. Oligomers IX and X are antisense compounds to the E2 region of the bovine papillonia virus-1 (BPV-1). The oligonucleotides were synthesized on either a 10 µmol scale in the "Trityl-On" mode. Standard deprotection conditions (30% NH$_4$OH, 55° C., 24 hours) were employed. The oligonucleotides were purified by reverse phase HPLC (Waters Delta-Pak C$_4$15 µm, 300A, 25×100 mm column equipped with a guard column of the same material). They were detritylated and further purified by size exclusion using a Sephadex G-25 column.

EXAMPLE 35
CONJUGATION OF OLIGONUCLEOTIDES AT THE 2'-POSITION: FUNCTIONALIZATION WITH BIOTIN

1. Single Site Modification

About 10 O.D. units ($A_{260}$) of Oligomer IX (see Example 34; approximately 60 nmols based on the calculated extinction coefficient of $1.6756 \times 10^5$) was dried in a microfuge tube. The oligonucleotide was dissolved in 200 µl of 0.2M $NaHCO_3$ buffer and D-biotin-N-hydroxysuccinimide ester (2.5 mg, 7.3 µmols) (Sigma, St. Louis, Mo.) was added followed by 40 µl DMF. The solution was let stand overnight. The solution was; applied to a Sephadex G-25 column (0.7×15 cm) and the oligonucleotide fractions were combined. Analytical HPLC shoed nearly 85% conversion to the product. The product was purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 mins., linear (1%) increase in B every minute thereafter) and further desalted on Sephadex G-25 to give the oligonucleotide conjugate:

Oligomer XI: CTG TCT CCA* TCC TCT TCA CT wherein A* represents a nucleotide functionalized to incorporate a biotin functionality linked via a 2'-carbamate amino linking group at the 2'-position of the designated nucleotide.

2. Multiple Site Modification

About 10 O.D. units ($A_{260}$) of oligomer X (see Example 34, approximately 60 nmols) was treated utilizing the method of Example 8 with D-biotin-N-hydroxysuccinimide ester (5 mg) in 300 µl of 0.2M $NaHCO_3$ buffer/50l DMF. Analytical HPLC showed 65% of double labeled oligonucleotide product and 30% of single labeled products (from the two available reactive sites. HPLC and Sephadex G-25 purification gave the oligonucletide:

Oligomer XII: CTG TCT CCA* TCC TCT TCA* CT wherein A* represents nucleotides functionalized to incorporate a biotin functionality linked via a 2'-carbamate aminolinker group to the 2'-position of the designated nucleotide.

EXAMPLE 36
ASSAY REAGENTS SYNTHESIS

1. Synthesis of Oligonucleotide-Disuccinimidyl Suberate (DSS) Conjugate

An aliquot (10 O.D. units, 60 nmols) of Oligomer IX (Example 34) is evaporated to dryness and is dissolved in freshly prepared 0.1M $NaHCO_3$/50 nM EDTA (100 µl, pH 8.25). The solution is then treated with a solution of DSS (Pierce Chemical Co., Rockford, Ill.) (2.6 mg, 7 µmol) in 200 µl DMSO. The solution is stored at room temperature for 15 minutes and then immediately applied to a Sephadex G-25 column (1×40 cm) that is previously packed and washed with water at 4° C. The oligonucleotide fractions are combined immediately in a 25 ml pear-shaped flask and are rapidly frozen in dry ice/isopropyl alcohol and lyophilized to a powder.

2. Synthesis of Oligonucleotide-Protein (Alkaline Phosphatase) Conjugate

A solution of calf intestinal alkaline phosphatase (Boehringer Mannheim) (20.6 mg, 2.06 ml, 147 nmol) is spun at 4° C. in a Centricon microconcentrator at 600 rpm until the volume is less than 50 µl. It is then redissolved in 1 ml of cold Tris buffer (pH 8.5, 0.1M containing 0.1 NaCl and 0.05M $MgCl_2$) and concentrated twice more. Finally, the concentrate is dissolved in 400 µl of the same buffer. This solution is added to the activated oligonucleotide from Previous Example and the solution is stored at room temp. The product is diluted to approximately 30 ml and applied to a Sephadex G-25 column (1×20 cm, chloride form) maintained at 4° C. The column is eluted with 50 nM Tris-Cl pH 8.5 until the UV absorbance of the fractions eluted reach near zero values. The column is then eluted with a NaCl salt gradient 0.05M to 0.75M (150 ml each) The different peaks are assayed for both oligonucleotide and alkaline phosphatase activity and the product bearing fractions are combined. Typically the first peak will be excess enzyme, the second peak the oligonucleotide-protein conjugate and the third peak unreactied oligonucletide. Isolation of the product from the product-bearing fractions via HPLC and desalting on Sephadex G-25 will yield an oligonucleotide of the sequence:

Oligomer XIII: CTG TCT CCA* TCC TCT TCA CT wherein A* represents a nucleotide functionalized to incorporate an alkaline phosphatare functionality linked via a 2'-carbamate-aminolinker-sulfo-SMCC (sulfosuccinimidyl-4-(N-maleimidomethyl)cyclohexane-1-carboxylate) linking group to the 21'-position of the designated nucleotide.

EXAMPLE 37

NUCLEASE PROTEIN-CONJUGATED OLIGONUCLEOTIDES

As in Example 36, oligomer IX is reacted with DSS reagent The isolated oligonucleotide-disuccinimidyl suberate conjugate is then further reacted with a lysine containing Nuclease RNase H using the method of Example 36. This will give an oligonucleotide of the structure:

Oligomer XIII: CCC AGG CUC AGA*-31'-protein (SEQ ID NO:8)

wherein protein represents RNase H.

EXAMPLE 38

INTERNALLY PROTEIN-CONJUGATED 2'- DERIVATIZED OLIGONUCLEOTIDES

Utilizing the method of Example 36 the amino linker oligonucleotide of Example 34 (oligomer IX) is reacted with DSS reagent The isolated oligonucleotide-disuccinimidyl suberate conjugate is then further reacted with a lysine containing staphylococcal Nuclease using the method of Example 36 . This will give an oligonucleotide of the structure:

Oligomer XIV: CCC A*GG CUC AGA wherein protein represents Staphylococcal Nuclease, the subscript "s" represents a phosphorothioate inter-nucleotide backbone linkage.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for modulating the production of a protein by an organism comprising contacting an organism with a compound comprising a plurality of linked nucleosides, wherein:

each nucleoside includes a ribofuranosyl sugar portion and a base portion, and at least one of said nucleosides bears at a 2'-O-position or a 3'-O-position a substituent having formula:

$$-R_A-N-C(X)-O-R_{1a}$$

or $$-C(X)-N(R_{1b})(R_{1c})$$

where:

$R_A$ is alkyl having from 1 to about 10 carbon atoms or $(CH_2-CH_2-Q)_x$;

$R_{1a}$ is alkenyl having 2 to about 10 carbon atoms;

$R_{1b}$ and $R_{1c}$, independently, are H, $R_2$, $R_A$, an amine protecting group or have formula $R_A-N(R_{1d})(R_{1e})$, $C(X)-R_2$, $C(X)-R_A-R_2$, $C(X)-Q-R_AR_2$, or $C(X)-Q-R_2$;

$R_{1d}$ and $R_{1e}$, independently, are H, $R_2$, $R_A$, an amine protecting group or have formula $C(X)-R_2$, $C(X)-R_A-R_2$, $C(X)-Q-R_A-R_2$, or $C(X)-Q-R_2$;

$R_2$ is asteroid molecule, a reporter molecule, alipophilic molecule, a reporter enzyme, a peptide, a protein, includes folic acid, or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)$OR_A$, C(O)$R_4$, $R_A-N_3$, or $R_A-NH_2$;

$R_4$ is Cl, Br, I, $SO_2R_5$ or has structure:

$$-{}^+S\overline{\phantom{X}}(CH_2)_m;$$

m is 2 to 7; and $R_5$ alkyl having 1 to about 10 carbon atoms.

2. A method for modulating the production of a protein by an organism comprising contacting an organism with a compound comprising a plurality of linked nucleosides, wherein:

each nucleoside includes a ribofuranosyl sugar portion and a base portion; and at least one of said nucleosides includes a pyrimidine base which bears at its 5-position a substituent having formula:

$$-R_A-O-C(X)-N(R_{1b})(R_{1c})$$

where:

$R_A$ is alkyl having from 1 to about 10 carbon atoms or $(CH_2-CH_2-Q)_x$;

$R_{1b}$ and $R_{1c}$, independently, are H, $R_2$, $R_A$, an amine protecting group or have formula $R_A-N(R_{1d})(R_{1e})$, $C(X)-R_2$, $C(X)-R_A-R_2$, $C(X)-Q-R_A-R_2$, or $C(X)-Q-R_2$;

$R_{1d}$ and $R_{1e}$, independently, are H, $R_2$, $R_A$, an amine protecting group or have formula $C(X)-R_2$, $C(X)-R_A-R_2$, $C(X)-Q-R_A-R_2$, or $C(X)-Q-R_2$;

$R_2$ is a steroid molecule, a reporter molecule, a lipophilic molecule, a reporter enzyme, a peptide, a protein, includes folic acid, or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)O$R_A$, C(O)$R_4$, $R_A$—$N_3$, or $R_A$—$NH_2$;

$R_4$ is Cl, Br, I, $SO_2R_5$ or has structure:

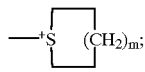

m is 2 to 7; and $R_5$ alkyl having 1 to about 10 carbon atoms.

3. A method of treating an animal having a disease characterized by undesired production of protein comprising contacting said animal with a compound comprising a plurality of linked nucleosides, wherein:

each nucleoside includes a ribofuranosyl sugar portion and a base portion; and at least one of said nucleosides bears at a 2'-O-position or a 3'-O-position a substituent having formula:

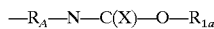

or

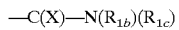

where:

$R_A$ is alkyl having from 1 to about 10 carbon atoms or $(CH_2—CH_2—Q)_x$;

$R_{1a}$ is alkenyl having 2 to about 10 carbon atoms;

$R_{1b}$ and $R_{1c}$, independently, are H, $R_2$, $R_A$, an amine protecting group or have formula $R_A$—N($R_{1d}$)($R_{1e}$), C(X)—$R_2$, C(X)—$R_A$—$R_2$, C(X)—Q—$R_A$—$R_2$, or C(X)—Q—$R_2$;

$R_{1d}$ and $R_{1e}$, independently, are H, $R_2$, $R_A$, an amine protecting group or have formula C(X)—$R_2$, C(X)—$R_A$—$R_2$, C(X)—Q-$R_A$—$R_2$, or C(X)—Q—$R_2$;

$R_2$ is a steroid molecule, a reporter molecule, a lipophilic molecule, a reporter enzyme, a peptide, a protein, includes folic acid, or has formula —Q—(CH$_2$CH$_2$—Q—)$_x$—$R_3$;

X is O or S;

each Q is, independently, is NH, O, or S;

x is 1 to about 200;

$R_3$ is H, $R_A$, C(O)OH, C(O)O$R_A$, C(O)$R_4$, $R_A$—$N_3$, or $R_A$—$NH_2$;

$R_4$ is Cl, Br, I, $SO_2R_5$ or has structure:

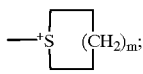

m is 2 to 7; and $R_5$ alkyl having 1 to about 10 carbon atoms.

4. A method of treating an animal having a disease characterized by undesired production of protein comprising contacting said animal with a compound comprising a plurality of linked nucleosides, wherein:

each nucleoside includes a ribofuranosyl sugar portion and a base portion; and at least one of said nucleosides includes a pyrimidine base which bears at its 5-position a substituent having formula:

where:

$R_A$ is alkyl having from 1 to about 10 carbon atoms or $(CH_2—CH_2—Q)_x$;

$R_{1b}$ and $R_{1c}$, independently, are H, $R_2$, $R_A$, an amine protecting group or have formula $R_A$—N($R_{1d}$)($R_{1e}$), C(X)—$R_2$, C(X)—$R_A$—$R_2$, C(X)—Q—$R_A$—$R_2$, or C(X)—Q—$R_2$;

$R_{1d}$ and $R_{1e}$, independently, are H, $R_2$, $R_A$, an amine protecting group or have formula C(X)—$R_2$, C(X)—$R_A$—$R_2$, C(X)—Q—$R_A$—$R_2$, or C(X)—Q—$R_2$;

$R_2$, is a steroid molecule, a reporter molecule, a lipophilic molecule, a reporter enzyme, a peptide, a protein, includes folic acid, or has formula—Q—(CH$_2$CH$_2$—Q—)$_x$—$R_3$;

X is O or S;

each Q is, independently, is NH, O, or S;

x is 1 to about 200;

$R_3$ is H, $R_A$, C(O)OH, C(O)O$R_A$, C(O)$R_4R_A$, —$N_3$, or $R_A$—$NH_2$;

$R_4$ is Cl, Br, I, $SO_2R_5$ or has structure:

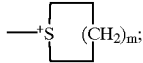

m is 2 to 7; and $R_5$ alkyl having 1 to about 10 carbon atoms.

* * * * *

UNITED STATES PATENT AND TRADEMARK OFFICE
CERTIFICATE OF CORRECTION

PATENT NO. : 6,322,987 B1
DATED : November 27, 2001
INVENTOR(S) : Cook et al.

It is certified that error appears in the above-identified patent and that said Letters Patent is hereby corrected as shown below:

Column 2,
Line 41, please delete "35" before the word disulfide;

Column 9,
Line 5, please delete "3mL" and insert therefor -- 30mL --;
Line 11, please delete "$CH_2CH_2$" and insert therefor -- $CH_2Cl_2$ --;

Column 10,
Line 59, please delete "Df" and insert therefor -- of --;

Column 14,
Line 38, please delete "endotheliomausing" and insert therefor -- endothelioma --;

Column 17,
Line 2, please delete "UD" and insert therefor -- up --;
Line 27, please delete "CFO" and insert therefor -- CPG --;

Column 19,
Line 30, please delete "buffer/50l" and insert therefor -- buffer/50μl --;

Column 20,
Line 37, please delete "-31'-protein" and insert therefor -- -3'-protein --;

Column 26,
Line 19, please insert the formula -- $R_A$-O-C(X)-N($R_{1b}$)($R_{1c}$) --;

Signed and Sealed this

Eighteenth Day of June, 2002

*Attest:*

*Attesting Officer*

JAMES E. ROGAN
*Director of the United States Patent and Trademark Office*